United States Patent [19]
O'Neill et al.

[11] Patent Number: 5,572,998
[45] Date of Patent: *Nov. 12, 1996

[54] METHOD OF SCANNING THE SPINE OF A PATIENT TO DETERMINE BONE DENSITY ALONG TWO DIFFERENT AXES

[75] Inventors: William O'Neill, Ann Arbor, Mich.; James R. Warne, Washington, Pa.

[73] Assignee: Hologic, Inc., Waltham, Mass.

[ * ] Notice: The portion of the term of this patent subsequent to Jan. 22, 2008, has been disclaimed.

[21] Appl. No.: 295,171

[22] Filed: Aug. 22, 1994

Related U.S. Application Data

[63] Continuation of Ser. No. 947,247, Sep. 18, 1992, abandoned, which is a continuation-in-part of Ser. No. 360,347, Jun. 5, 1989, Pat. No. 5,165,410, which is a continuation-in-part of Ser. No. 204,513, Jun. 9, 1988, abandoned, which is a continuation-in-part of Ser. No. 50,726, May 15, 1987, abandoned.

[51] Int. Cl.$^6$ ..................................................... A61B 6/00
[52] U.S. Cl. ........................... 128/653.1; 378/55; 378/197
[58] Field of Search ................................. 128/653.1, 659; 378/54–56, 119, 146, 193, 195–198

[56] References Cited

U.S. PATENT DOCUMENTS

| | | | |
|---|---|---|---|
| 3,803,417 | 4/1974 | Kok | 378/197 |
| 3,944,830 | 3/1976 | Dissing | 378/55 |
| 3,988,585 | 10/1976 | O'Neill et al. | 250/363 |
| 4,012,636 | 3/1977 | Engdahl et al. | 250/363 |
| 4,107,532 | 8/1978 | MaCovski | 250/360 |
| 4,144,457 | 3/1979 | Albert | 250/445 |
| 4,275,305 | 6/1981 | Racz et al. | 250/445 |
| 4,342,916 | 8/1982 | Jatteau et al. | 378/4 |
| 4,358,856 | 11/1982 | Steivender et al. | 378/167 |
| 4,365,343 | 12/1982 | Grady et al. | 378/181 |
| 4,495,645 | 1/1985 | Ohhashi | 382/6 |
| 4,590,678 | 5/1986 | Platz | 250/363 |
| 4,618,133 | 10/1986 | Siczek | 269/323 |
| 4,649,560 | 3/1987 | Grady et al. | 378/197 |
| 4,653,083 | 3/1987 | Rossi | 378/196 |
| 4,716,581 | 12/1987 | Barud | 378/197 |
| 4,829,549 | 5/1989 | Vogel et al. | 378/55 |
| 4,856,044 | 8/1989 | Tanguy et al. | 378/193 |
| 4,947,414 | 8/1990 | Stein | 378/55 |
| 4,986,273 | 1/1991 | O'Neill et al. | 128/653.1 |

FOREIGN PATENT DOCUMENTS

| | | |
|---|---|---|
| 0253742 | 7/1987 | European Pat. Off. . |
| 0265302 | 9/1987 | European Pat. Off. . |
| 2238706 | 2/1974 | Germany . |
| 24 12 161.7 | 3/1974 | Germany . |
| WO86/07531 | 12/1986 | WIPO . |
| WO90/10859 | 9/1990 | WIPO . |

OTHER PUBLICATIONS

Wahner et al. "Assement of Bone Mineral. Part 1"*J. Nuclear Medicine* 25(10):1134–1141 (1984).

Mazess, "Dual Photon Absorptiometry and Osteoporosis–Absorptiometric Instrumentation" Meeting publication.

Jacobson, Final Progress Report, "Development of Dichrmography Techniques", pp. 1–2 and 15 –18 (May 31, 1968).

Rutt, B. K., et al., "High Speed, High–Precision Dual Photon Absorptiometry", Reprint of pester exhibited at meeting at the American Society of Bone and Mineral Research, Jun. 16, 1985, Washington, D.C.

(List continued on next page.)

*Primary Examiner*—Ruth S. Smith
*Attorney, Agent, or Firm*—Hamilton, Brook, Smith & Reynolds, P.C.

[57] ABSTRACT

A method of scanning the spine of a patient in which radiation is directed through the spine from a source and received by a detector to measure bone density of the spine. Multidirectional scanning is accomplished by rotating the radiation source and detector about the spine of the patient being scanned to provide both A-P and lateral scanning for imaging and bone density measurements.

8 Claims, 2 Drawing Sheets

OTHER PUBLICATIONS

Pearce, R. B., "DPA Gaining Strength in Bone Scanning Debate", *Diagnostic Imaging* (Jun. 1986).

Norland Corporation advertising brochure OsteoStatus System pp. 1–8.

"A New Dimension in Dual–Photon Absorptiometry Novo Introduces the BMC–Lab 23", Light Years Ahead.

Lunar Radiation Corporation's Users Manual for Lunar DP3 Dual Photon Scanner.

Brochure, "Osteotek Bone Densitometry", Medical & Scientific Enterprises, Inc.

Sartoris, D. J. et al., "Trabecular Bone Density in the Proximal Femur: Quantitative CT Assessment", *Radiology*, 160:707–712 (1986).

Mazess, R. B., et al., "Spine and Femur Density Using Dual–Photon Absorptiometry in US White Women", *Bone and Mineral*, 2:211–219 (1987).

Weissberger, M. A., et al., "Computed Tomography Scanning for the Measurement of Bone Mineral in the Human Spine", *Journal of Computer Assisted Tomography*, 2:253–262 (Jul. 1978).

Genant, H., "Assessing Osteoporosis: CT's Quantitative Advantage", *Diagnostic Imaging*, (Aug. 1985).

METHOD OF SCANNING THE SPINE OF A PATIENT TO DETERMINE BONE DENSITY ALONG TWO DIFFERENT AXES

This application is a continuation application of U.S. Ser. No. 07/947,247 filed on Sep. 18, 1992, now abandoned, which is a continuation-in-part application of U.S. Ser. No. 07/360,347 filed on Jun. 5, 1989, now U.S. Pat. No. 5,165, 410, which is a continuation-in-part application of U.S. Ser. No. 07/204,513 filed on Jun. 9, 1988, now abandoned, which is a continuation-in-part application of U.S. Ser. No. 07/050, 726 filed on May 15, 1987, now abandoned.

BACKGROUND OF THE INVENTION

This invention relates to radiologic measuring devices, and more particularly, to the use of radiation in measuring bone structure.

The diagnostic use of radiation in evaluating bone structure has recently been applied in assessing bone demineralization that occurs with advancing age. Bone mineral is lost from all parts of the skeleton, and at a linear rate from the lumbar spine, starting at about 35 years of age. The resultant demineralization results in a high risk of fractures with an increased associated mortality and morbidity. In evaluation of the spine, there is a very good correlation between dual photon densitometry measurements of bone density and fracture resistance in excised vertebrae subjected to compression testing. It is also important to evaluate mineral loss in the hip, as appendicular losses often match or exceed spine loss in patients over 70.

Dual photon absorptiometry enables non-invasive quantitative analysis of bone mineral in regions of the body that were previously inaccessible using single photon absorptiometry. The use of two photon energies minimizes errors that result from irregular body contour and soft tissue inhomogeneities. Essentially, two photon energies are necessary to allow discrimination of two substances of a given system. In this case between bone mineral and soft tissue. The most commonly used photon energies in dual photon scanning are 44 and 100 KeV. The measurements of the attenuation of this radiation as it passes through the body yields the bone mineral density.

SUMMARY OF THE INVENTION

The present invention involves the multidirectional measurement of human bone densities for diagnostic purposes. A radiation source, and a detector used for measuring the radiation transmitted through the object being measured, are rigidly aligned by a bracket or arm. This detector is mounted in a telescoping mechanism to permit control over the source/detector distance. The arm and the attached source and detector, are mounted on an "x-y" table that permits scanning of objects over a predetermined planar area. This apparatus is mounted so that the source, detector, and scanning mechanism can be rotated to view a stationary object from different angles.

In a preferred embodiment of the invention, the pivot axis about which the arm rotates is displaceable so that the source will clear the table upon rotation. The rotating apparatus may be mounted in a drawer with guides or rails that telescope out to support the system during rotation. The rotating elements are weighted so that very little pressure is necessary to rotate the system. The weight is distributed so that if the mechanism is stopped at any point during rotation, it will at most slowly accelerate under its own weight. If the center of gravity of the rotating mechanism is approximately along the pivot axis, this condition will be met. One weight is placed in the detector to vertically adjust the center of gravity. A second weight is placed adjacent the scanning assembly to horizontally adjust the center of gravity.

DETAILED DESCRIPTION OF THE INVENTION

Existing scanner assemblies used in bone densitometry generally permit unidirectional scanning of patients only. To obtain lateral or side views, for example, the patient must be turned. This movement of the patient is often difficult or impossible depending upon their physical condition.

Figure 1:
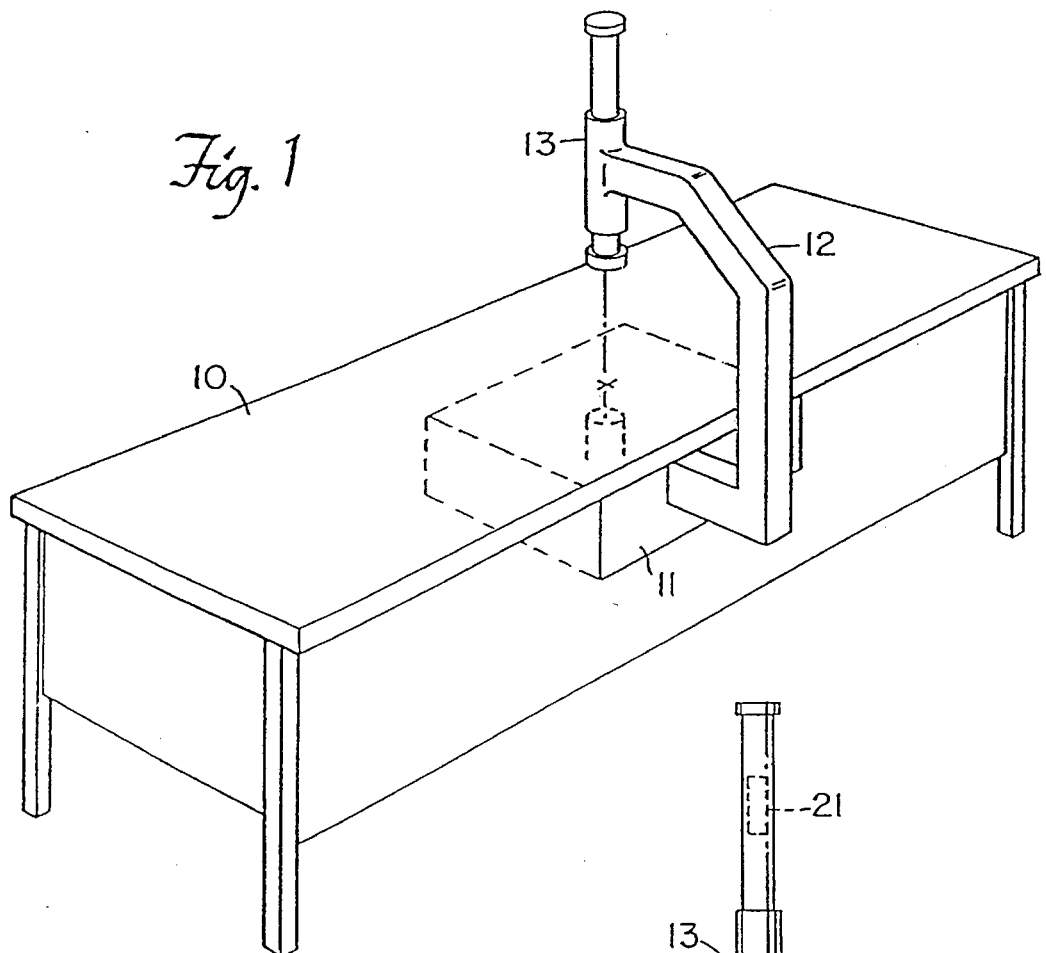
FIG. 1 is a perspective view of the bone densitometer.
Figure 2:
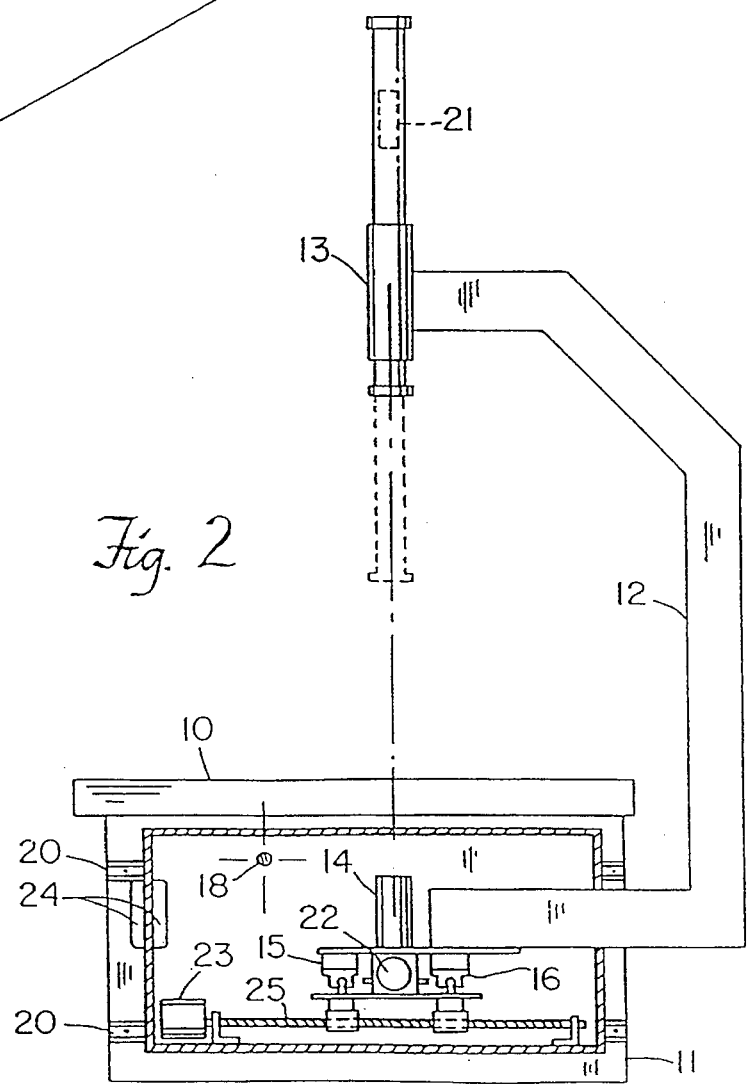
FIG. 2 is a side view of the radiation source and detector in the interior position.

A dual photon bone densitometer used in diagnosing osteoporosis is illustrated generally in FIG. 1. A table 10 on which the patient lies has a drawer assembly 11 which is pulled out from under the table on the side from which a bracket 12 protrudes. The bracket 12 extends in a "C" shape from the drawer assembly 11 to a detecting apparatus 13. FIG. 2 shows, in a cross-sectional view, the relationship between the detector 13 and the contents of the drawer assembly 11.

A radiation source 14 is mounted on a moveable platform 15. The source 14 is rigidly aligned with the detector 13 by bracket 12 to insure that radiation emitted from the source is received by the detector regardless of the angle to which the source-detector axis is rotated. The entire rotatable apparatus is mounted on a tray or "saddle" 17. The saddle 17 is rotatably mounted onto the assembly plates 19. The plates 19 in one embodiment constitute the side walls of a drawer which compactly houses the source and scanning apparatus.

Figure 3:
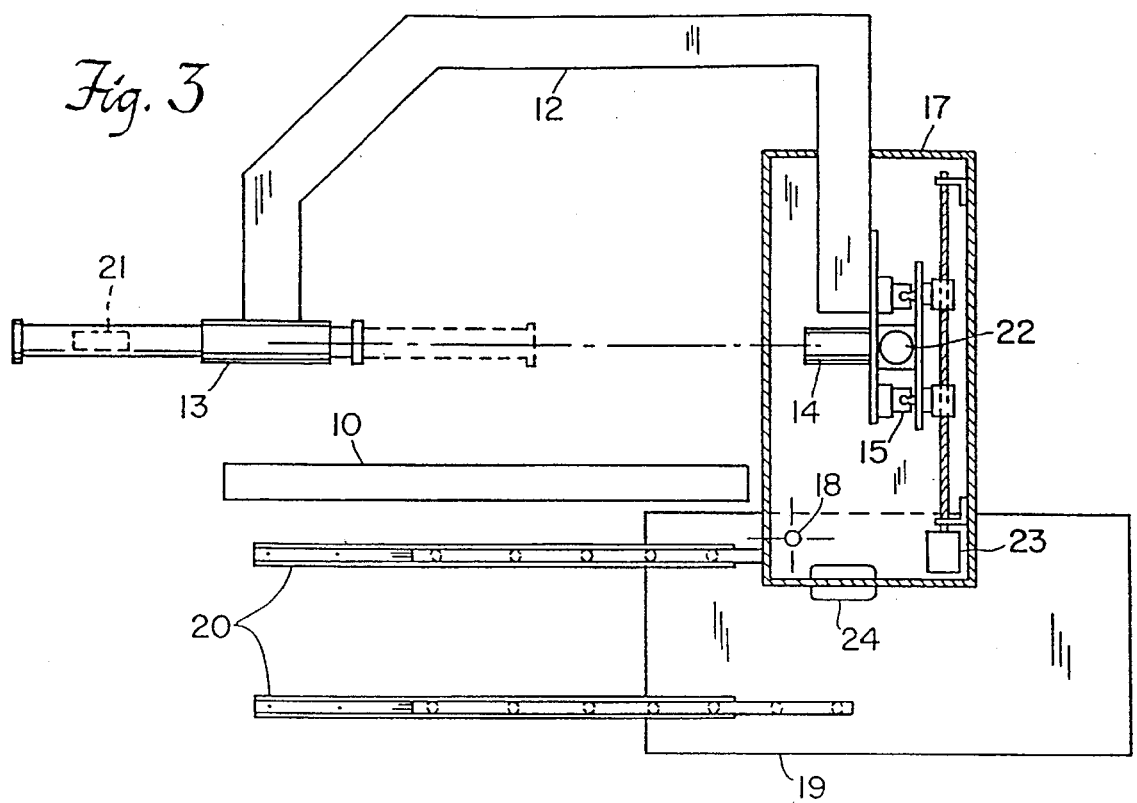
FIG. 3 is a side view of the apparatus rotated to the lateral position.

To rotate the apparatus from the anterior position shown in FIG. 2 to the lateral position shown in FIG. 3, the following steps must be taken. The user releases a locking mechanism and pulls the arm horizontally to one side of the table so that the saddle 17 and plates 19 slide the source from under the center of the table to avoid contact with the table during rotation. In one embodiment of the invention the source is approximately one inch below the table during anterior scanning and thus cannot be rotated without lateral movement. Source proximity to the table is desirable, as the source and detector are preferably as close to one another as possible to yield the best possible image. The drawer assembly plates 19 telescope out along the glides 20 until the pivot point 18 is astride the table 10. The plates 19 are then locked in position by a locking mechanism (not shown). The arm 12 and the attached source and saddle assembly 17 are rotated manually by the user about the axis 18 to the desired position. Note that the pivot axis location must be chosen so that the source and scanning apparatus are rotated into a position just above the plane of the table. This insures that objects positioned on the table can be fully scanned laterally. The pivot location also affects the adjustment of the center of gravity as discussed below. In an alternative embodiment of the invention, the lateral movement of the drawer assembly and/or the rotation may be automatically controlled by adding the necessary motor and control systems.

FIGS. 2 and 3 also illustrate the presence of weights 21 and 24. After initial assembly of the apparatus, the center of gravity of the rotating elements must be adjusted to assure ease of manual rotation. In a preferred embodiment of the invention, the center of gravity of the rotating elements is located along the pivot axis 18. When the center of gravity is so situated the rotating elements will not accelerate under their own weight when the bracket 12 is rotated to any chosen angle, stopped and released.

Figure 4:
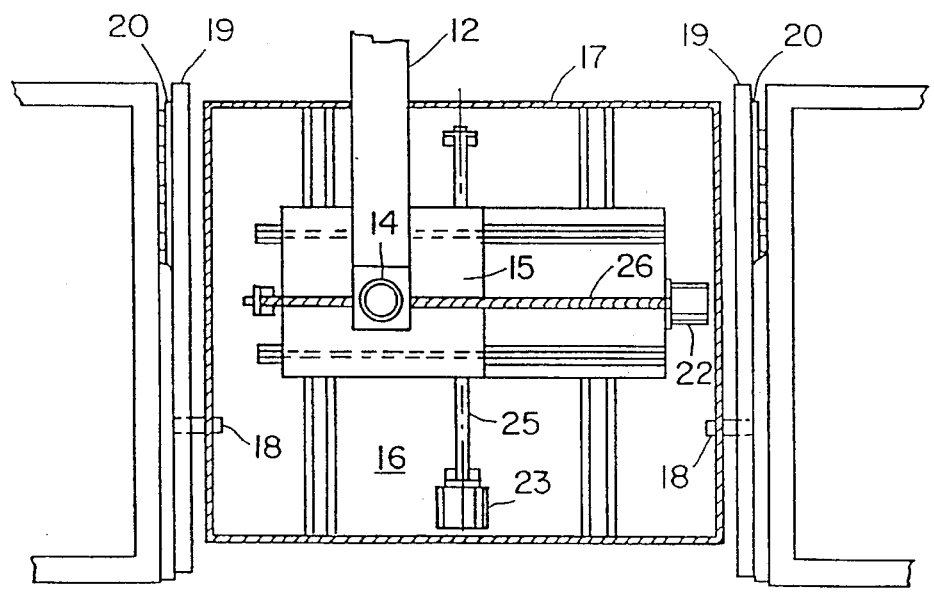
FIG. 4 is a top view of the saddle and drawer assembly.

FIG. 4 shows a top view of the drawer assembly 11 and illustrates the location of the pivot axis 18, the glides 20 for displacement of the plates 19, and the tracks 26 on which the platform 15 rides. The platform 15, as well as the attached source 14, bracket 12, and detector 13, are moved in a plane perpendicular to the source-detector axis. The driving mechanism for the scanning motion is a so-called "x-y" table 16. The scanning mechanism is comprised of threaded bars, one running along the longitudinal or "y" axis 26 of the table, the second 25 running perpendicular to the first across the width or "x" axis of the table. The platform 15 has threaded housings which receive, and are driven by, the two threaded bars. The threaded "x" bar 25 is rotated by a motor 23 and the threaded "y" bar 26 is rotated by the motor 22. When the scanning assembly is rotated along with the source and detector, this insures full scanning capability at any angle. In a preferred embodiment of the invention, the scanning mechanism is controlled automatically by feeding the scanning rate and the size of the area to be scanned into a computer, which then triggers the radiation source and coordinates the desired scan.

During initial rotation of the system from the vertical position, the weight of the saddle and enclosed elements controls the balancing of the bracket 12 and the attached components. The weights 24 are added to the front wall of the saddle to adjust the center of gravity in the horizontal plane. The weight 21 is added to the detector system to adjust the center of gravity in the vertical plane. As the system is rotated through larger angles from the vertical (e.g. 45°–90°), the correct weighting of the bracket and detector by weight 21 becomes more important to maintain ease of manual rotation.

By rotating the detector arm, scanning of the lumbar spine in both the anterior and lateral projections is now possible without repositioning the patient. The patient remaining in the supine position for both the lateral and anterior-posterior projection maintains the correct alignment of both projections, permits direct correlation of the two studies, and anatomically is diagnostically correct.

Performing the lateral image as the first study may enable the physician to observe extra-osseous calcification in tissue overlying the lumbar spine. In the anterior-posterior projections, such extra-osseous calcification cannot be distinguished from bone, and could therefore interfere with accurate bone density measurements in that projection. The bone being studied may be examined in real time by amplifying the signal output from the detector and displaying it on a C-T screen.

While the invention has been particularly shown and described with reference to preferred embodiments thereof, it will be understood by those skilled in the art that various changes in form and details may be made without departing from the spirit and scope of the invention as defined in the appended claims.

We claim:
1. A method of scanning the spine of a patient comprising:
positioning a human patient on a support surface, the spine of the patient extending along an axis of the support surface;
providing a C-shaped member mounted relative to the support surface, the C-shaped member rigidly aligning a radiation source and detector and being selectively driven in a first direction along the axis of the support surface by a motor;
scanning a region of a patient's spinal column at a first angle with the C-shaped member, source and detector to detect with the detector radiation at two energies that is transmitted through the region from the source while the C-shaped member is being driven along the axis of the support surface by the motor, the source emitting radiation at said two energies;
determining bone density in the spinal column from radiation detected with the detector at the two energies during the scanning at the first angle;
rotating the C-shaped member, the radiation source and detector about the support surface to a second angle such that the source and detector are aligned laterally through the spinal region at an angle different from the first angle;
scanning a region of the spinal column with the C-shaped member, source and detector, the detector receiving radiation from the source that is transmitted laterally through the region to the detector at the second angle while the C-shaped member is being driven along the axis of the support surface by the motor; and
generating an image of the scanned region of the spinal column on a display from at least one of: (1) radiation detected with the detector at the first angle; and (2) radiation detected with the detector at the second angle.
2. The method of claim 1 further comprising scanning the patient's hip with the source and detector.
3. The method of claim 1 further comprising automatically controlling scanning of the spinal column with scan parameters in a computer.
4. The method of claim 1 comprising displacing the C-shaped member to one side of the spinal region after scanning at the first angle and before rotating the C-shaped member to the second angle.
5. A method of scanning a region of a patient's lumbar spine comprising:
positioning a human patient on a support surface, the lumbar spine of the patient extending along an axis of the support surface;
providing a C-shaped member mounted relative to the support surface, the C-shaped member rigidly aligning a radiation source and a detector in a vertical plane and being selectively driven in a first direction along the axis of the support surface by a motor, and selectively causing relative displacement between the support surface and the C-shaped member in a second direction that is perpendicular to the support surface axis;
scanning a region of the patient's lumbar spine at a first angle with the C-shaped member to detect with the detector radiation at two energies that is transmitted in the vertical plane through the region from the source that emits radiation at said two energies, the C-shaped member being driven by the motor to scan along the axis of the support surface;
determining bone density in the lumbar spine from radiation detected with the detector at the two energies during the scanning at the first angle;

rotating the C-shaped member, the radiation source and the detector in the vertical plane about the support surface to a second angle such that the source and detector are aligned laterally through the region of the lumbar spine at an angle different from the first angle;

scanning a region of the lumbar spine with the C-shaped member, source and detector such that the detector detects radiation from the source that is transmitted laterally through the region to the detector while the C-shaped member is being driven in the first direction along the axis of the support surface at the second angle; and generating and displaying an image of a scanned region of the lumbar spine on a display from radiation detected with the detector at least at one of: (1) the scanning at the first angle; and (2) the scanning at the second angle.

6. The method of claim 5 including the step of displacing said C-shaped member laterally relative to said support surface in a direction perpendicular to the axis of the support surface, between said scanning at said first angle and the scanning at the second angle.

7. The method of claim 6 further comprising laterally displacing the C-shaped member with a second motor.

8. The method of claim 6 further comprising providing rails to support the C-shaped member relative to the support surface during lateral displacement of the C-shaped member.

* * * * *